(12) United States Patent
Choi

(10) Patent No.: US 12,042,404 B2
(45) Date of Patent: Jul. 23, 2024

(54) INTERBODY FUSION CAGE SURGERY SYSTEM

(71) Applicant: TECHCORD CO., LTD., Daejeon (KR)

(72) Inventor: Young Kyu Choi, Daejeon (KR)

( * ) Notice: Subject to any disclaimer, the term of this patent is extended or adjusted under 35 U.S.C. 154(b) by 410 days.

(21) Appl. No.: 17/628,330

(22) PCT Filed: Jun. 3, 2021

(86) PCT No.: PCT/KR2021/006923
§ 371 (c)(1),
(2) Date: Jan. 19, 2022

(87) PCT Pub. No.: WO2021/256745
PCT Pub. Date: Dec. 23, 2021

(65) Prior Publication Data
US 2022/0280312 A1    Sep. 8, 2022

(30) Foreign Application Priority Data
Jun. 17, 2020    (KR) .................... 10-2020-0073462

(51) Int. Cl.
*A61F 2/46*    (2006.01)
*A61B 1/00*    (2006.01)
(Continued)

(52) U.S. Cl.
CPC ........ *A61F 2/4611* (2013.01); *A61B 1/00066* (2013.01); *A61B 1/00126* (2013.01);
(Continued)

(58) Field of Classification Search
CPC .............. A61B 17/7076; A61B 17/708; A61B 17/7085; A61B 17/7035; A61B 1/317; A61B 1/00096; A61B 1/00105; A61B 1/05; A61B 1/0676; A61B 1/00066; A61B 1/00126; A61B 1/042; A61B 1/3135; A61B 1/0669; A61B 1/0684; A61B 1/07; A61B 90/06; A61B 90/10; A61B 90/14; A61B 90/361; A61B 2017/00296; A61F 2/46; A61F 2/4657; A61F 2/4684; A61F 2/4603; A61F 2/4611; A61F 2/4455; A61F 2/4465; A61F 2/4637; A61F 2002/30261;
(Continued)

(56) References Cited

U.S. PATENT DOCUMENTS

| | | | | |
|---|---|---|---|---|
| 2013/0245633 A1* | 9/2013 | Dauster | ............... | A61B 17/708 606/279 |
| 2015/0342757 A1* | 12/2015 | Lomeli | ............... | A61B 90/10 623/17.16 |
| 2017/0332886 A1* | 11/2017 | Choi | ............... | A61B 1/00094 |

FOREIGN PATENT DOCUMENTS

| | | |
|---|---|---|
| JP | 2014-512883 A | 5/2014 |
| JP | 2018-531058 A | 10/2018 |

(Continued)

*Primary Examiner* — Marcela I. Shirsat
(74) *Attorney, Agent, or Firm* — KORUS Patent, LLC; Seong Il Jeong

(57) ABSTRACT

The cage handle with an endoscope function of the present invention is equipped with a lens and an optical cable so that a surgeon can perform an interbody fusion cage surgery, viewing the image of the front of a cage accurately, clearly. Since a separate endoscope or X-ray is not used, the surgery can be performed more easily, efficiently, and economically.

4 Claims, 6 Drawing Sheets

(51) Int. Cl.
    *A61B 1/04*     (2006.01)
    *A61B 1/05*     (2006.01)
    *A61B 1/06*     (2006.01)
    *A61B 1/07*     (2006.01)
    *A61B 1/313*     (2006.01)
    *A61B 1/317*     (2006.01)
    *A61B 17/00*     (2006.01)
    *A61B 17/70*     (2006.01)
    *A61B 90/00*     (2016.01)
    *A61F 2/30*     (2006.01)
    *A61F 2/44*     (2006.01)

(52) U.S. Cl.
    CPC ............ *A61B 1/042* (2013.01); *A61B 1/0669* (2013.01); *A61B 1/0684* (2013.01); *A61B 1/07* (2013.01); *A61B 1/317* (2013.01); *A61F 2/4455* (2013.01); *A61B 1/00096* (2013.01); *A61B 1/00105* (2013.01); *A61B 1/05* (2013.01); *A61B 1/0676* (2013.01); *A61B 1/3135* (2013.01); *A61B 2017/00296* (2013.01); *A61B 17/7076* (2013.01); *A61B 90/361* (2016.02); *A61F 2002/30593* (2013.01); *A61F 2/4603* (2013.01); *A61F 2002/4627* (2013.01); *A61F 2002/4629* (2013.01); *A61F 2002/4635* (2013.01); *A61F 2/4684* (2013.01); *A61F 2002/4696* (2013.01)

(58) Field of Classification Search
    CPC .... A61F 2002/30593; A61F 2002/4658; A61F 2002/4627; A61F 2002/448; A61F 2002/4629; A61F 2002/4635; A61F 2002/4638; A61F 2002/4696
    USPC .......................................................... 606/99
    See application file for complete search history.

(56) References Cited

FOREIGN PATENT DOCUMENTS

| | | |
|---|---|---|
| KR | 10-2011-0081224 A | 7/2011 |
| KR | 10-1681451 B1 | 11/2016 |
| KR | 10-1852973 B1 | 5/2018 |

\* cited by examiner

Prior Art

Prior Art

INTERBODY FUSION CAGE SURGERY SYSTEM

FIELD OF THE INVENTION

The present invention relates to an interbody fusion cage surgery system, and more specifically, to an interbody fusion cage surgery system that embodies an endoscopic function in a cage handle so that a surgeon can clearly view an insertion path and surrounding affected areas when performing an interbody fusion surgery that inserts a cage into the spine.

BACKGROUND OF THE INVENTION

Spinal fusion is surgery to fix vertebrae by inserting a cage into a space where the damaged disc of the spine has been removed or affected vertebrae in the case of spondylolysis. The body of the cage has small holes and a spiral protrusion like a screw. The cage is generally made of titanium or retinol and manufactured by a 3D printer. For inserting the cage into the spine, the upper and lower vertebrae of the target disk are ground a little, and then the cage in which the bone chip is inserted, is fixed to the cage handle by turning the cage like a screw, or is attached to the dedicated handle and firmly inserted into the cage Clean version of the substitute specification handle. The cage immobilizes the upper and lower vertebrae at first, but after 3 to 4 months, the bones grow in the cage, and the upper and lower vertebrae are naturally attached to each other.

Historically, the spinal fusion surgery has been performed by making a relatively large incision in the back of a patient to access a surgical site. More recently, a small incision is made in a space where surgical tools can be used, and the surgery is performed by inserting a cage through this space. However, when inserting the cage into the incision site, the surgeon cannot see or confirm the insertion path through an endoscope, and thus, the cage is inserted relying on the sense of the surgeon.

Referring to FIGS. 6A to 6C, FIG. 6A shows a conventional cage handle H' used to insert a cage. FIG. 6B is a magnified view of the front tip of the cage handle H' shown in FIG. 6A. FIG. 6C is a drawing showing a cage C' positioned on the disk using the cage handle H'.

For performing the spinal fusion surgery using the conventional cage handle H', a surgeon needs to view an X-ray screen while inserting the cage into the affected area, or makes a hole in the waist and inserts an endoscope to see the cage C'. However, since the surgeon cannot view the position of the spinal nerve, the surgery requires a very high level of attention and Clean version of the substitute specification caution when the cage C' is initially inserted into the body. Accordingly, relying only on X-ray images may cause many problems.

FIG. 7 is a cross-sectional view of an endoscope 1' disclosed in Registered Patent No. 10-1681451 of the applicant of this invention. The endoscope 1' includes a tube 100'; a working channel 130' that occupies most of the space of the tube 100' and through which a surgical tool passes; a camera or lens 110' and a cleaning channel 120' formed on a lower part of the working channel 130', and an optical fiber 140' disposed in the remaining space of the lower part and functioning as a light source.

The present invention discloses a remarkably improved structure of a cage handle by combining the function of an endoscope with a cage handle. From another point of view, the present invention relates to a novel endoscope structure for spinal fusion surgery that can be used by directly attaching a cage thereto.

DETAILED DESCRIPTION OF THE INVENTION

Technical Problems

Therefore, the object of the present invention is to provide a dedicated cage handle or endoscope, and a system including the same that enable a surgeon to insert a cage into an affected area, viewing if there is a nerve or an obstacle in the Clean version of the substitute specification insertion area during the spinal fusion surgery, by embodying a compact endoscopic camera on the front of the cage.

SUMMARY OF THE INVENTION

To achieve the first object of the present invention, one embodiment of the present invention provides a cage handle for spinal fusion surgery, the cage handle comprising: a rotating knob rotatable and positioned in a center of the cage handle; a tube extended forward from a front side of the rotating knob; a coupling part positioned at a front end of the tube for coupling with a cage and including a screw thread formed on an outer surface thereof for coupling with the cage; a lens installed on at least an inner center of the coupling part; an optical fiber surrounding and arranged on an outer circumference of the lens, and the cage surrounding and mounted on an outer circumference of the optical fiber, wherein the cage handle is connected to a camera connector and a LED connector, or the camera connector and an optical cable of a light source device, through a cable.

The cage may include a passage passing through a front side and a rear side thereof, and the passage may be coupled to the coupling part.

The cage may be an open type, and include: a cage front tip part tapered toward a center of a front side thereof; a cage Clean version of the substitute specification coupling part continuously extended from a back of the cage front tip part and having a screw thread on an outer surface thereof, and a cage sleeve part continuously extended from a back of the cage coupling part and having an unthreaded outer surface thereof, wherein the coupling part of the cage handle has a structure corresponding to that of the cage, and the coupling part includes: a front tip part tapered toward a center of a front side thereof; a coupling part continuously extended from a back of the front tip part and having a screw thread on an outer surface thereof, and a sleeve continuously extended from a back of the coupling part and having an unthreaded outer surface thereof, wherein by inserting the front tip part of the cage handle into the passage of the cage and turning the cage handle to gradually advance the cage handle, the screw thread of the cage handle is engaged with the screw thread of the cage coupling part.

In addition, the present invention provides a spinal fusion cage surgery system comprising: a cage handle, a console connected to the cage handle through a cable and equipped with a camera connector and an LED connector, and a display for displaying an image transmitted from the cage handle.

Technical Effects of the Invention

According to the present invention, the cage handle and the system for spinal fusion surgery allow a surgeon to see the affected area accurately and clearly during spinal surgery. In addition, the cage of the cage handle and the system is easily attachable, and thus, the cage handle and the system can be used as economical surgery tools.

BEST MODE FOR THE INVENTION

Hereinafter, the present invention will be described in more detail in conjunction with the accompanying drawings and the embodiments described below. Objects and effects of the present invention and technical configurations for achieving them will become apparent with reference to the drawings and the embodiments. In the description of the present invention, if detailed descriptions of a well-known function or configuration unnecessarily obscures the gist of the present invention, the detailed description thereof will be omitted.

Throughout the specification, when a part "includes" a certain element, it means that other elements may be further included, rather than excluding other elements, unless otherwise stated. Meanwhile, in an embodiment of the present invention, each of functional blocks or means, and components may be composed of one or more sub-components.

Figure 1:
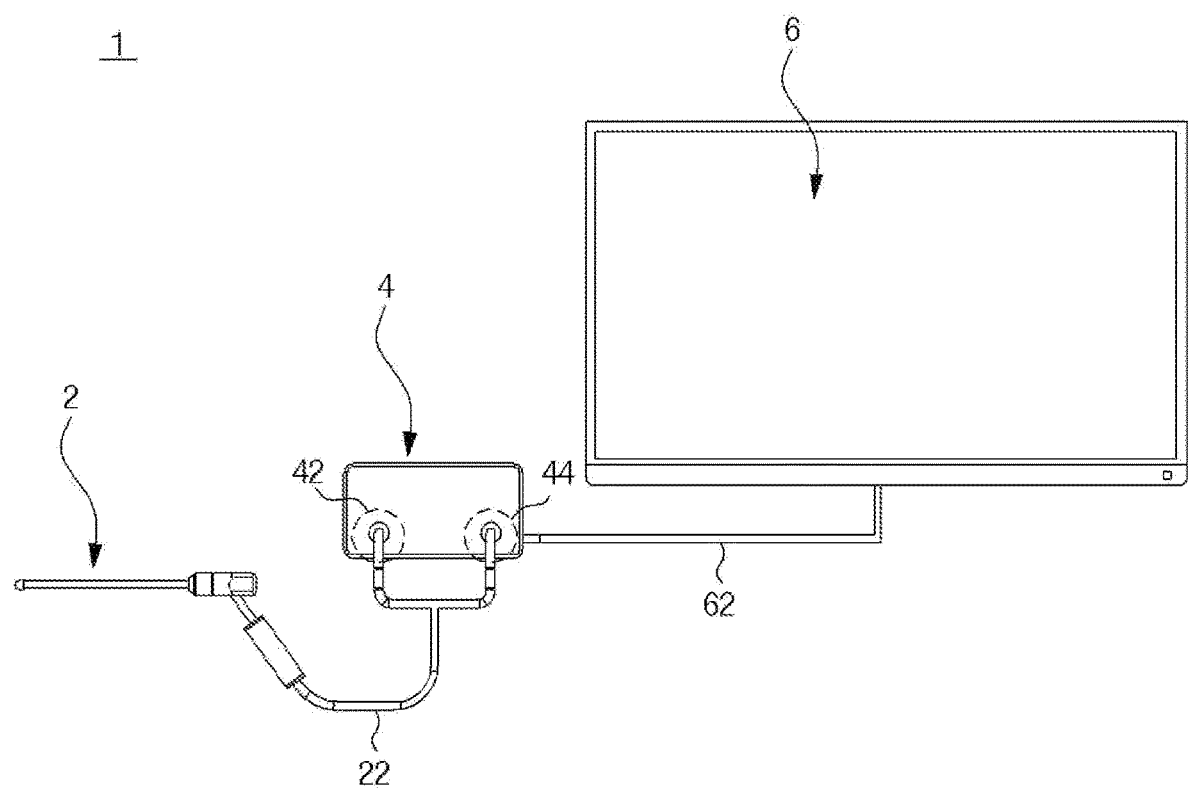
FIG. 1 is an entire configuration of an interbody fusion cage surgery system according to an embodiment of the present invention.

FIG. 1 is an entire configuration of an interbody fusion cage surgery system 1 according to an embodiment of the present invention.

Referring to FIG. 1, a cage handle 2 that also functions as an endoscope is connected to a console 4 through a cable 22. A camera connector 42 and an LED connector 44 are installed in the console 4, and the console 4 is connected to a display 6 through a cable 62 for surgery monitoring. The cage handle 2 may be connected to an optical cable of a light source device instead of the LED connector 44.

Figure 2:
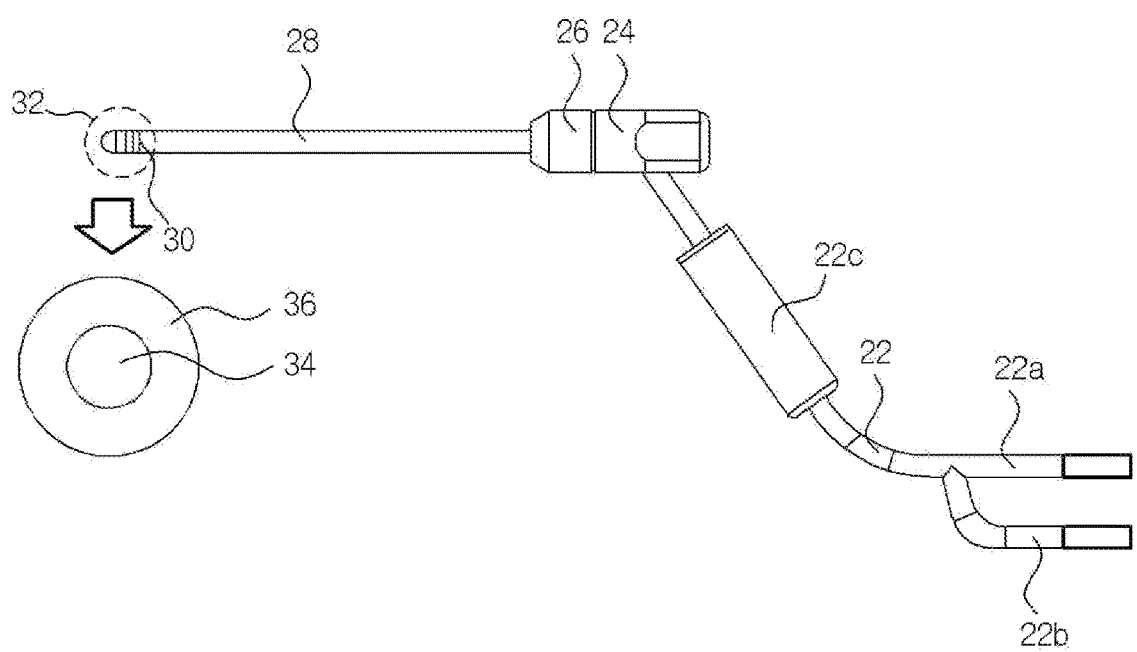
FIG. 2 is an entire configuration of a cage handle according to an embodiment of the present invention.

FIG. 2 is an entire configuration of a cage handle 2 according to an embodiment of the present invention.

Referring to FIG. 2, a control knob is positioned in the center of the cage handle 2 and includes a rotating knob 26 and a fixed knob 24 adjacent to the rotating knob 26. The rotating knob 26 is connected with a cylindrical tube 28 extended forward from the front side of the rotating knob 26, that is, extended to the left in FIG. 2. A coupling part 30 for coupling with a cage C is provided at the front end of the tube 28. A screw thread 32 for coupling with the cage C is formed on the outer surface of the coupling part 30. Meanwhile, the fixed knob 24 is connected to the cable 22, which is extended from the bottom side of the fixed knob Clean version of the substitute specification 24. A grip part 22c for holding the cage handle 2 by hand is installed on the path of the cable 22, and the cable 22 passing through the grip part 22c branches into a camera cable 22a connected to the camera connector 42 and an LED cable 22b connected to the LED connector 44.

As shown in the magnified cross-sectional view of the coupling part 30, a lens 34 is installed in the inner center of the coupling part 30, and an optical fiber 36 is installed on the coupling part 30, surrounding an outer circumference of the lens 34. Since the cage handle 2 of the present invention is a tool for inserting the cage C into the spine, a working channel and a cleaning channel provided in a general endoscope are not required. Therefore, since the lens 34 is installed in the center of the coupling part 30 and the optical fiber 36 is closely arranged around the lens 34, a surgeon can monitor the inside of the target area of patient's body on a larger and clearer screen during the surgery.

In the embodiment mentioned above, the tool is referred to as a "cage handle", but from another point of view, it may also be referred to as an endoscope with an attachable cage for interbody fusion surgery.

Figure 3:
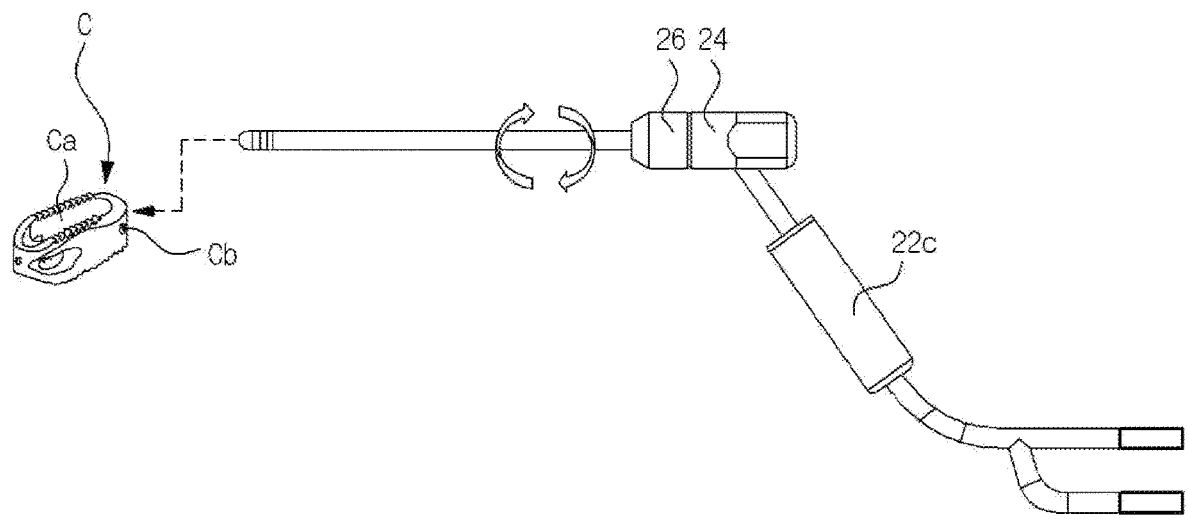
FIG. 3 is a drawing for explaining a function of the cage handle of the present invention.

FIG. 3 is a drawing for explaining a function of the cage handle 2 of the present invention.

Referring to FIG. 3, the cage C is equipped with a bone chip, which is to be attached to the bone in the human body, through a square through-hole Ca formed on the central top side thereof, and includes a passage Cb passing through the front side and rear side thereof. The passage Cb is an element to which the coupling part 30 is coupled. The rotating knob 26 is rotatable clockwise and counterclockwise. For example, when the rotating knob 26 is turned clockwise, the coupling part 30 gradually enters into the passage Cb of the cage C, and thus, the two members can be coupled. When the rotating knob 26 is turned counterclockwise, the coupling part 30 gradually comes out from the passage Cb of the cage C, and thus, the two members are separated from each other.

Figure 4:
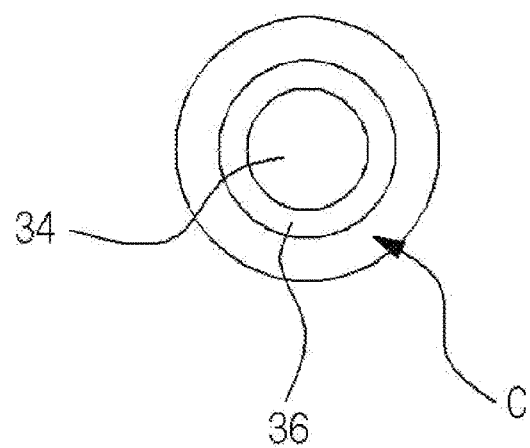
FIG. 4 is a cross-sectional view of a coupling part on which a cage is mounted according to an embodiment of the present invention.

FIG. 4 is a cross-sectional view of the coupling part 30 on which the cage C is mounted according to an embodiment of the present invention. Referring to FIG. 4, the cage C is mounted on the outermost circumference of the optical fiber 36, surrounding the optical fiber 36. Since the lens 34 and the optical fiber 36 are disposed as close to the cage C as possible to occupy most of the area of the inner center of the cage C, and pass through the inside of the cage C to be disposed in the front of the cage C, the optical fiber 36 can extensively illuminate and the lens 34 can clearly capture the dark and long inside of the surgical site.

Figure 5A:
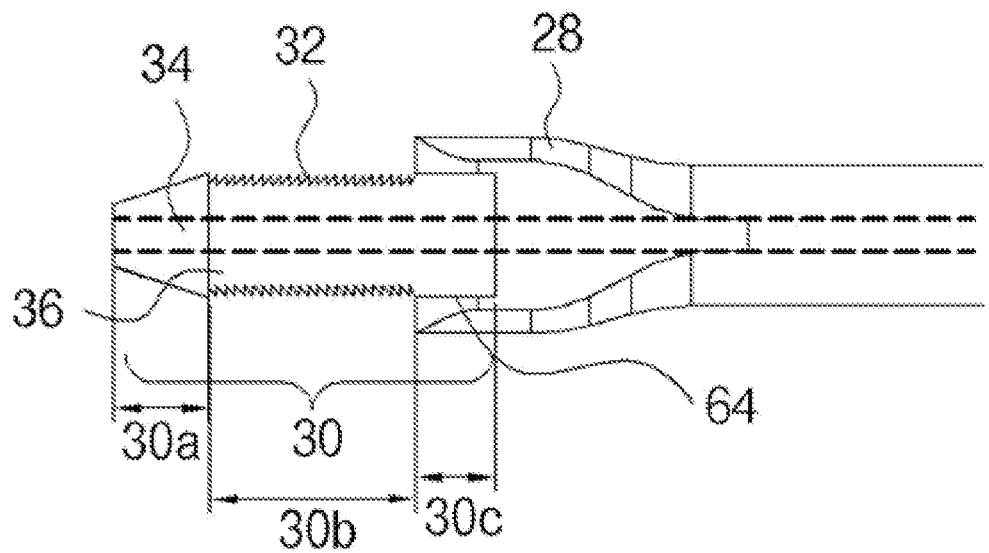
FIGS. 5A and 5B are drawings for explaining in detail an example of the coupling part of the cage handle and the cage mounted thereto according to an embodiment of the present invention.
Figure 5B:
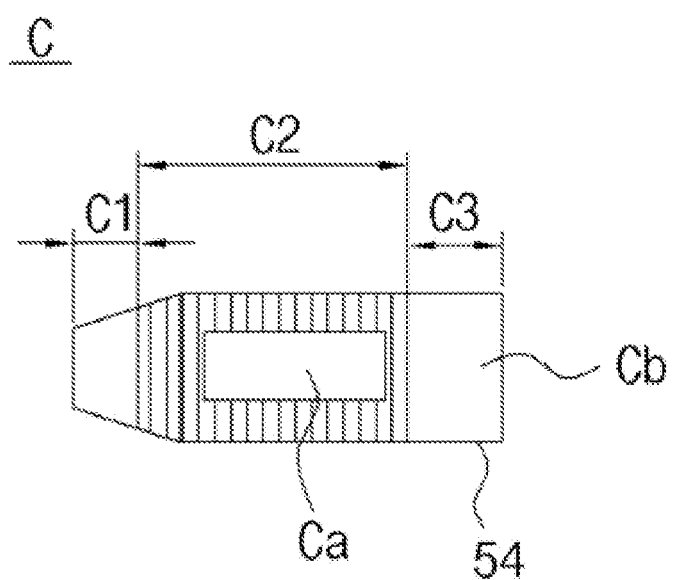
Figure 6A:
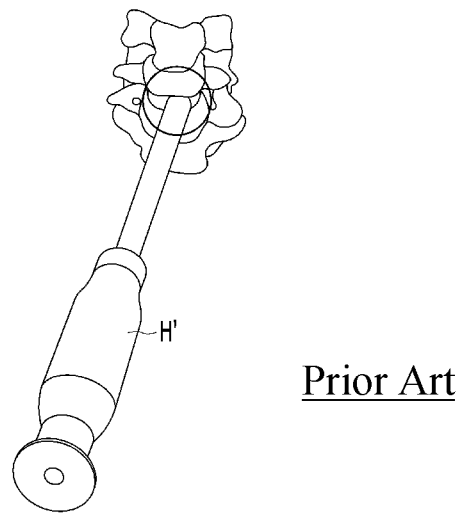
FIGS. 6A to 6C are drawings illustrating a conventional cage handle and an operation using the conventional cage handle according to prior arts.
Figure 6B:
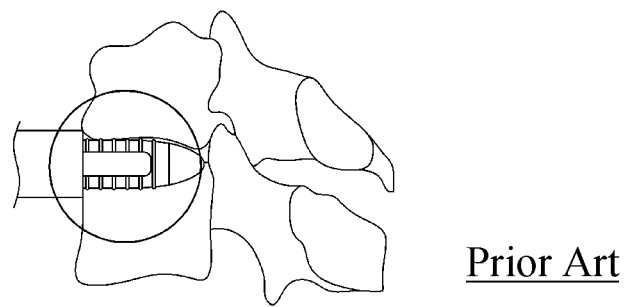
Figure 6C:
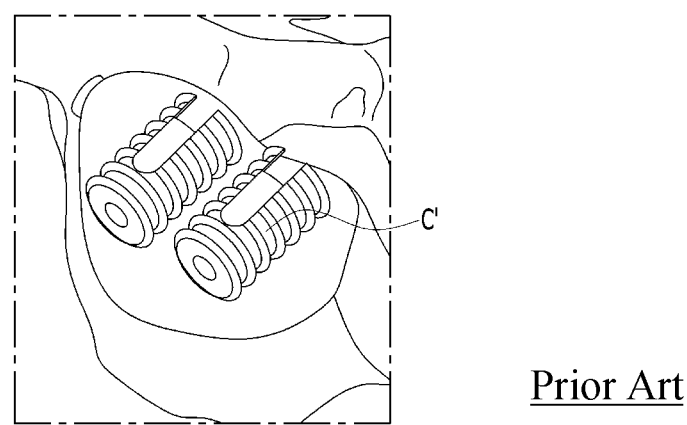
Figure 7:
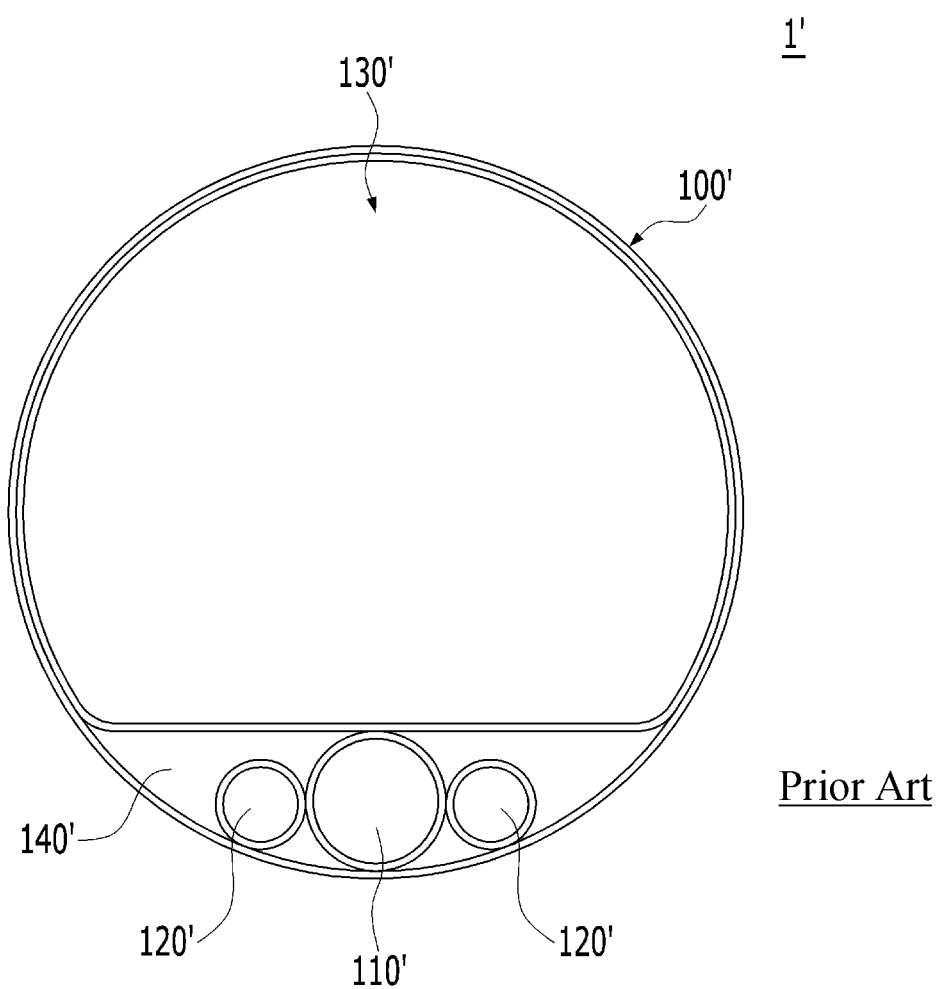
FIG. 7 is a cross-sectional view of a conventional endoscope according to prior arts.

FIGS. 5A and 5B are drawings for explaining in detail an example of the coupling part 30 of the cage handle 2 and the cage C mounted thereto according to an embodiment of the present invention.

Referring to FIGS. 5A and 5B, the cage C is an open type, and includes: a cage front tip part C1 tapered toward the center of the front, a cage coupling part C2 continuously extended from the back of the cage front tip part C1 and having a screw thread on the outer surface, and a cage sleeve part C3 continuously extended from the back of the cage coupling part C2 and having an unthreaded outer surface 54. The coupling part 30 of the cage handle 2 has a structure corresponding to that of the cage C. Specifically, the coupling part 30 includes a front tip part 30a tapered toward the center of the front, a coupling part 30b continuously extended from the back of the front tip part 30a and having a screw thread 32 on the outer surface, and a sleeve 30c continuously extended from the back of the cage coupling part 30*b* and having an unthreaded outer surface 64. For coupling between the cage C and the cage handle 2, the front tip part 30*a* of the cage handle 2 is inserted into the passage Cb of the cage C. Then, by turning the cage handle 2 clockwise, for example, the cage handle 2 is gradually advanced, and the screw thread 32 of the cage handle 2 is fully engaged and lock-coupled with the screw Clean version of the substitute specification thread of the cage coupling part C2, thereby enabling the cage C to be coupled to the cage handle 2. Accordingly, the lens 34 and the optical fiber 36 are accommodated in the cage front tip part C1 of the cage C, and the front side of the lens 34 and the optical fiber 36 are exposed to the outside. This structure enables the optical fiber 36 to illuminate the surgical site and the lens 34 to capture an image of it. The cage sleeve C3 of the cage C is inserted into the gap between the inner side and the outer side of the tube 20 so that the cage C is fixed to the cage handle 2.

The coupling part 30 may be integrally molded with the tube 28 or may be manufactured and supplied separately from the tube 28. Depending on the type of cage C, the shape of the coupling part 30 may also be changed to correspond thereto.

In some embodiments, the cage surgery system 1 of the present invention can be variously applied to the joint of the neck disc as well as the waist and the back.

What is claimed is:

1. A cage handle for spinal fusion surgery, the cage handle comprising:
    a rotating knob rotatable and positioned in a center of the cage handle;
    a tube extended forward from a front side of the rotating knob;
    a coupling part positioned at a front end of the tube for coupling with a cage and including a screw thread formed on an outer surface thereof for coupling with the cage;
    a lens installed on at least an inner center of the coupling part;
    an optical fiber surrounding and arranged on an outer circumference of the lens, and
    the cage surrounding and mounted on an outer circumference of the optical fiber,
    wherein the cage handle is connected to a camera connector and a LED connector, or the camera connector and an optical cable of a light source device, through a cable.

2. The cage handle of claim 1, wherein the cage includes a passage passing through a front side and a rear side thereof, and the passage is coupled to the coupling part.

3. The cage handle of claim 2, wherein the cage is an open type, and includes:
    a cage front tip part tapered toward a center of a front side thereof;
    a cage coupling part continuously extended from a back of the cage front tip part and having a screw thread on an outer surface thereof, and
    a cage sleeve part continuously extended from a back of the cage coupling part and having an unthreaded outer surface thereof,
    wherein the coupling part of the cage handle has a structure corresponding to that of the cage, and the coupling part includes:
    a front tip part tapered toward a center of a front side thereof;
    a coupling part continuously extended from a back of the front tip part and having a screw thread on an outer surface thereof, and
    a sleeve continuously extended from a back of the coupling part and having an unthreaded outer surface thereof,
    wherein by inserting the front tip part of the cage handle into the passage of the cage and turning the cage handle to gradually advance the cage handle, the screw thread of the cage handle is engaged with the screw thread of the cage coupling part.

4. A spinal fusion cage surgery system comprising:
    a cage handle of claim 1;
    a console connected to the cage handle through a cable and equipped with a camera connector and an LED connector, and
    a display for displaying an image transmitted from the cage handle.

* * * * *